US010449003B2

(12) United States Patent
Reid et al.

(10) Patent No.: US 10,449,003 B2
(45) Date of Patent: Oct. 22, 2019

(54) INDIVIDUALIZED PREOPERATIVE PLANNING SYSTEM AND METHOD

(71) Applicant: The Penn State Research Foundation, University Park, PA (US)

(72) Inventors: John Spence Reid, Hummelstown, PA (US); Gregory S. Lewis, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 75 days.

(21) Appl. No.: 15/577,078

(22) PCT Filed: May 31, 2016

(86) PCT No.: PCT/US2016/034978
§ 371 (c)(1),
(2) Date: Nov. 27, 2017

(87) PCT Pub. No.: WO2016/196443
PCT Pub. Date: Dec. 8, 2016

(65) Prior Publication Data
US 2018/0168731 A1 Jun. 21, 2018

Related U.S. Application Data

(60) Provisional application No. 62/168,128, filed on May 29, 2015.

(51) Int. Cl.
*G06K 9/00* (2006.01)
*A61B 17/56* (2006.01)
(Continued)

(52) U.S. Cl.
CPC ............. *A61B 34/10* (2016.02); *G16H 50/50* (2018.01); *A61B 34/25* (2016.02); *A61B 2034/102* (2016.02); *A61B 2034/108* (2016.02)

(58) Field of Classification Search
USPC ....... 382/100, 103, 106, 128–133, 154, 162, 382/172, 173, 181, 199, 209, 219, 232,
(Continued)

(56) References Cited

U.S. PATENT DOCUMENTS 8,126,234 B1 2/2012 Edwards et al.
8,335,616 B2 12/2012 Neal et al.
(Continued)

OTHER PUBLICATIONS

Fengjiao Guan, Application of Optimization Methodology and Specimen-Specific Finite Element Models for Investigating Material Properties of Rat Skull, Annals of Biomedical Engineering, Jan. 2011, pp. 85-95, vol. 39, No. 1, State Key Laboratory of Advanced Design and Manufacturing for Vehicle Body, Hunan University, Hunan, China; Bioengineering Center, Wayne State University, 818 W. Hancock, Detroit, accepted Jul. 5, 2010; published online Jul. 23, 2010).

(Continued)

*Primary Examiner* — Seyed H Azarian
(74) *Attorney, Agent, or Firm* — Dinsmore & Shohl LLP

(57) ABSTRACT

An individualized preoperative planning system for fracture fixation constructs provides fracture assessment before automatically performing finite element simulations to generate biomechanics associated with a large number of fracture fixation construct design alternatives. Data visualization utilizing multivariate plots or surrogate modeling based on the simulation results are then provided to surgeons enabling surgeons to view, adjust and optimize their fracture fixation construct designs.

18 Claims, 21 Drawing Sheets

(51) Int. Cl.
  *A61B 34/10* (2016.01)
  *G16H 50/50* (2018.01)
  *A61B 34/00* (2016.01)

(58) Field of Classification Search
  USPC .... 382/254, 276, 284–294, 305, 312; 700/1; 715/850; 606/70; 623/20.35
  See application file for complete search history.

(56) References Cited

U.S. PATENT DOCUMENTS

| | | | | |
|---|---|---|---|---|
| 9,603,711 | B2* | 3/2017 | Bojarski | A61B 17/155 |
| 2006/0195198 | A1* | 8/2006 | James | A61B 90/36 |
| | | | | 700/1 |
| 2010/0268097 | A1 | 10/2010 | Hatib et al. | |
| 2012/0163683 | A1* | 6/2012 | Wilson | A61B 5/4504 |
| | | | | 382/128 |
| 2013/0073272 | A1 | 3/2013 | Wallace et al. | |
| 2013/0211531 | A1* | 8/2013 | Steines | A61F 2/4684 |
| | | | | 623/20.35 |
| 2015/0324114 | A1* | 11/2015 | Hurley | A61B 17/8066 |
| | | | | 715/850 |
| 2015/0327896 | A1* | 11/2015 | Bottlang | A61B 17/8047 |
| | | | | 606/70 |

OTHER PUBLICATIONS

Timothy W. Simpson, Approximation Methods in Multidisciplinary Analysis and Optimization: A Panel Discussion, the discussion at the Approximation Methods Panel that was held at the 9th AIAA/ISSMO Symposium on Multidisciplinary Analysis & Optimization, in Atlanta, GA, on Sep. 2-4, 2002.

Pavel E. Galibarov, A probabilistic modelling scheme for analysis of long-term failure of cemented femoral joint replacements, Proc IMechE Part H: J Engineering in Medicine 226(12), IMechE 2012, pp. 927-938, Downloaded from pih.sagepub.com at Univ of Michigan on Jun. 24, 2015.

\* cited by examiner

| Plate length ($L_{plate}$, cm) | Fracture gap ($d_{gap}$, cm) | Screw number ($N_{screws}$) | Screw position (symmetry) |
|---|---|---|---|
| 15.2 | | ①②③④⦙○○○○ | |
| | 0.2 | 1 | 1 / 3 |
| | | 2 | 1,3 |
| | 0.5, 1, 1.5, 2, 2.5, and 3 | 1 | 1 / 2 / 3 |
| | | 2 | 1,2 / 1,3 / 2,3 |
| | | 3 | 1,2,3 |
| 18.8 | | ①②③④⑤⦙○○○○ | |
| | 0.2 | 1 | 1 / 3 |
| | | 2 | 1,3 |
| | 0.5, 1, 1.5, 2, 2.5, and 3 | 1 | 1 / 3 / 4 |
| | | 2 | 1,3 / 1,4 / 3,4 |
| | | 3 | 1,2,4 |
| | | 4 | 1,2,3,4 |
| 22.4 | | ①②③④⑤⑥⦙○○○○ | |
| | 0.2 | 1 | 1 / 4 |
| | | 2 | 1,4 |
| | 0.5, 1, 1.5, 2, 2.5, and 3 | 1 | 1 / 3 / 5 |
| | | 2 | 1,3 / 1,5 / 3,5 |
| | | 3 | 1,3,5 |
| | | 5 | 1,2,3,4,5 |
| 26 | | ①②③④⑤⑥⑦⦙○○○○○○ | |
| | 0.2 | 1 | 1 / 3 / 5 |
| | | 2 | 1,3 / 1,5 / 3,5 |
| | | 3 | 1,3,5 |
| | 0.5, 1, 1.5, 2, 2.5, and 3 | 1 | 1 / 3 / 5 / 6 |
| | | 2 | 1,3 / 1,5 / 1,6 / 3,5 / 3,6 / 5,6 |
| | | 3 | 1,3,5 / 1,3,6 / 1,5,6 / 3,5,6 |
| | | 4 | 1,3,5,6 |
| | | 6 | 1,2,3,4,5,6 |
| 29.6 | | ①②③④⑤⑥⑦⑧⦙○○○○○○○ | |
| | 0.2 | 1 | 1 / 2 / 4 / 6 |
| | | 2 | 1,2 / 1,4 / 1,6 |
| | | 3 | 1,2,4 / 1,2,6 / 1,4,6 |
| | | 4 | 1,2,4,6 |
| | 0.5, 1, 1.5, 2, 2.5, and 3 | 1 | 1 / 2 / 4 / 6 / 7 |
| | | 2 | 1,2 / 1,4 / 1,6 / 1,7 |
| | | 3 | 1,2,4 / 1,2,6 / 1,2,7 / 1,4,6 / 1,4,7 / 1,6,7 |
| | | 4 | 1,2,4,6 / 1,2,4,7 / 1,2,6,7 / 1,4,6,7 |
| | | 5 | 1,2,4,6,7 |
| | | 7 | 1,2,3,4,5,6,7 |

FIG. 3

| Axial loading | | | | | | |
|---|---|---|---|---|---|---|
| Model selection method* | | Full quadratic | Significant regressors | R2-based selection (1%) | R2-based selection (5%) | Stepwise | Linear |
| $\sigma_{plate\_max}$ | #of Regressors R2 | 26 .90 | 6 0.89 | 6 0.90 | 4 0.90 | 9 0.90 | 6 0.82 |
| $\sigma_{screw}$ | Regressor# Rsquare | 26 0.95 | 9 0.95 | 5 0.95 | 3 0.91 | 12 0.95 | 6 0.79 |
| $k_{axial}$ | Regressor# Rsquare | 26 0.99 | 14 0.99 | 5 0.98 | 3 0.97 | 12 0.99 | 6 0.95 |
| $\epsilon_{shear}$ | Regressor# Rsquare | 26 0.84 | 6 0.83 | 5 0.83 | 3 0.81 | 6 0.83 | 6 0.56 |

| Torsion loading | | | | | | |
|---|---|---|---|---|---|---|
| Model selection method* | | Full quadratic | Significant regressors | R2-based selection (1%) | R2-based selection (5%) | Stepwise | Linear |
| $\sigma_{plate\_max}$ | Regressor# Rsquare | 26 .88 | 10 0.87 | 9 0.87 | 7 0.87 | 12 0.88 | 6 0.41 |
| $\sigma_{screw}$ | Regressor# Rsquare | 26 0.94 | 17 0.94 | 9 0.94 | 4 0.90 | 15 0.94 | 6 0.69 |
| $k_{torsion}$ | Regressor# Rsquare | 26 0.99 | 14 0.99 | 5 0.99 | 3 0.96 | 11 0.99 | 6 0.92 |
| $\epsilon_{shear}$ | Regressor# Rsquare | 26 0.88 | 10 0.75 | 9 0.76 | 4 0.74 | 10 0.76 | 6 0.56 |

FIG. 7

|  |  | Regression coefficient (p<0.0001) | | | | | | | |
|---|---|---|---|---|---|---|---|---|---|
|  |  | Axial loading | | | | Torsion loading | | | |
|  |  | $\sigma_{plate}$ (MPa) | $\sigma_{screw}$ (MPa) | $k_{axial}$ (N/mm) | $\varepsilon_{shear}$ (%) | $\sigma_{plate}$ (MPa) | $\sigma_{screw}$ (MPa) | $k_{torsion}$ (N mm/°) | $\varepsilon_{shear}$ (%) |
|  | $r^2$ | 0.90 | 0.91 | 0.97 | 0.77 | 0.87 | 0.90 | 0.96 | 0.76 |
|  | Intercept($\beta_0$) | -5.68 | 30.02 | 3560.79 | -10.48 | 81.30 | 65.29 | 1617.88 | 5.13 |
| Linear variable | $L_{plate}(\beta_1)$ | - | - | - | - | - | - | - | - |
|  | $d_{gap}(\beta_2)$ | - | - | - | - | - | - | - | -4.84 |
|  | $N_{screw}(\beta_3)$ | - | - | - | - | 5.78 | - | - | - |
|  | $L_{inner}(\beta_4)$ | 19.82 | 12.86 | -297.72 | 2.58 | 6.61 | 10.83 | -180.28 | 0.30 |
|  | $L_{outer}(\beta_5)$ | - | - | - | - | - | - | - | - |
|  | $E_{implant}(\beta_6)$ | 0.37 | - | - | - | - | - | 6.15 | - |
| Quadratic Variable | $L_{plate}^2(\beta_7)$ | - | - | - | - | - | - | - | - |
|  | $d_{gap}^2(\beta_8)$ | - | - | - | 1.50 | - | - | - | 1.13 |
|  | $N_{screw}^2(\beta_9)$ | - | 2.17 | - | - | - | - | - | - |
|  | $L_{inner}^2(\beta_{10})$ | -0.42 | - | 5.42 | - | 0.21 | - | 3.94 | - |
|  | $L_{outer}^2(\beta_{11})$ | - | - | - | - | - | - | - | - |
| $L_{plate}$ × | $d_{gap}(\beta_{12})$ | - | - | - | - | - | - | - | - |
|  | $N_{screw}(\beta_{13})$ | - | - | - | - | - | - | - | - |
|  | $L_{inner}(\beta_{14})$ | - | - | - | - | -0.24 | - | - | - |
|  | $L_{outer}(\beta_{15})$ | - | - | - | - | - | - | - | - |
|  | $E_{implant}(\beta_{16})$ | - | - | - | - | 0.008 | - | - | - |
| $d_{gap}$ × | $N_{screw}(\beta_{17})$ | - | - | - | - | - | - | - | - |
|  | $L_{inner}(\beta_{18})$ | - | - | - | -0.93 | - | - | - | - |
|  | $L_{outer}(\beta_{19})$ | - | - | - | - | - | - | - | - |
|  | $E_{implant}(\beta_{20})$ | - | - | - | - | - | - | - | - |
| $N_{screw}$ × | $L_{inner}(\beta_{21})$ | - | -4.28 | - | - | -1.10 | -3.09 | - | - |
|  | $L_{outer}(\beta_{22})$ | - | - | - | - | - | 0.46 | - | - |
|  | $E_{implant}(\beta_{23})$ | - | - | - | - | - | - | - | - |
| $L_{inner}$ × | $L_{outer}(\beta_{24})$ | - | - | - | - | - | -0.15 | - | - |
|  | $E_{implant}(\beta_{25})$ | - | - | - | - | -0.02 | - | - | -0.001 |
|  | $L_{outer}$ × $E_{implant}(\beta_{26})$ | -0.01 | - | 0.31 | - | - | - | - | - |

FIG. 8

| | | | |
|---|---|---|---|
| Axial loading | $\sigma_{plate\_max}$ (MPa) | $R^2=0.88$ | $-5.68 + 19.82L_{inner} + 0.37E_{implant} - 0.42L_{inner}^2 - 0.01L_{outer} \times E_{implant}$ |
| | $\sigma_{screw}$ (MPa) | $R^2=0.91$ | $30.02 + 12.86L_{inner} + 2.17N_{screws}^2 - 4.28N_{screws} \times L_{inner}$ |
| | $k_{axial}$ (N/mm) | $R^2=0.97$ | $3560.79 - 297.72L_{inner} + 5.42L_{inner}^2 + 0.31L_{outer} \times E_{implant}$ |
| | $\varepsilon_{shear}$ (%) | $R^2=0.81$ | $-10.48 + 2.58L_{inner} + 1.50d_{gap}^2 - 0.93d_{gap} \times L_{inner}$ |
| Torsion loading | $\sigma_{plate\_max}$ (MPa) | $R^2=0.87$ | $81.30 + 5.78N_{screws} \times L_{inner} + 6.61L_{inner} + 0.21L_{inner}^2 - 0.24L_{plate} \times L_{inner} + 0.008L_{plate} \times E_{implant}$ $-1.10N_{screws} \times L_{inner} - 0.02L_{inner} \times E_{implant}$ |
| | $\sigma_{screw}$ (MPa) | $R^2=0.90$ | $65.29 + 10.83L_{inner} - 3.09N_{screws} \times L_{inner} + 0.46N_{screws} \times L_{outer} - 0.15L_{inner} \times L_{outer}$ |
| | $k_{torsion}$ (N mm/°) | $R^2=0.96$ | $1617.88 - 180.28L_{inner} + 6.15E_{implant} + 3.94L_{inner}^2$ |
| | $\varepsilon_{shear}$ (%) | $R^2=0.74$ | $5.13 - 4.84d_{gap} + 0.30L_{inner} + 1.13d_{gap}^2 - 0.001L_{inner} \times E_{implant}$ |

FIG. 9

INDIVIDUALIZED PREOPERATIVE PLANNING SYSTEM AND METHOD

CROSS-REFERENCE TO RELATED APPLICATIONS

This application is a PCT application claiming the priority of U.S. Provisional Patent Application Ser. No. 62/168,128, filed May 29, 2015.

FIELD OF INVENTION

The present invention is generally related to methods and systems for patient-specific preoperative planning, specifically for orthopaedic surgeries such as fracture fixation implant surgical treatments.

BACKGROUND OF THE INVENTION

Orthopaedic trauma is a leading cost in healthcare. Human-computer interfaces hold promise to allow physicians to more readily visualize and interact with scientific and engineering data to improve medical surgeries and treatments. In orthopaedics, mechanics play an important role in determining clinical outcome (for example, implants can fail, and tissue strains affect healing), but for surgeries such as fracture fixation, 3D biomechanics can be complex. Currently surgeons are not able to readily visualize and optimize these 3D biomechanics, leading to suboptimal treatments, sometimes revisions surgeries, and time inefficiencies in planning and surgery execution in the operating room. Furthermore the training of surgeons is lacking in this area because there is currently no way to accurately visualize how the myriad of possible choices in a surgery affect variables such as stresses and strains. Currently clinicians operate on patients based largely on training, experience and intuition.

SUMMARY OF THE INVENTION

The present invention helps to determine the optimal orthopaedic surgery for a patient. In surgical repair of fractures, the surgeon must design a mechanical construct in a manner such that it provides adequate stability for healing and does not lead to implant failure.

In locked plate fracture fixation there are many available options in geometric configurations, sizes, and materials. These options include but are not limited to fracture plate length, number of screws, screw configurations, and fracture gap size. These variables affect stresses in the implants and stability of the fracture healing site, and strains in healing tissue can substantially affect fracture healing. To optimize fracture fixation surgeries and improve outcomes for patients, it is important to understand these biomechanical principles. However the three-dimensional biomechanics associated with locked plate fixation can be complex and involves interactions among the variables of the fixation design.

An individualized preoperative planning system according to the invention can be used by surgeons for designing fracture fixation implant surgeries based on individual patient data. The individualized preoperative planning system may include an input module for receiving the individual patient data such as imaging data of fracture injuries. The imaging data may include CT scan, MRI, or X-ray imaging. The individual patient data further includes bone density, bone shape, soft tissue anatomy, patient age, sex, weight, smoking status, and other data relevant for fracture fixation.

The individualized preoperative planning system may also process the patient data to provide a basis for finite element modeling of a series of possible fixation constructs for the fracture injury. This can use modeling directly from segmenting CT images, use of statistical shape models, or choice of a generic model from a library collection of such models which best matches the patient.

The system may also perform computer experiments such as parametric finite element simulations to characterize possible fracture fixation designs. The finite element model may be a novel image-based modularized-block finite element model.

The system is configured to receive the design parameters inputs and constraints from the surgeon and provide biomechanics output for the design to the surgeon.

The system may also develop surrogate models relating the design parameters to the biomechanics outputs.

The system may also be configured to map the biomechanics outputs graphically using 3D animated bodies and 3D field plots.

The system may also provide the capabilities to plot the design parameters and the biomechanics with multivariate plots, by which the user is able to specify data points or ranges by clicking within the multivariate plots and the computer is able to identify the fracture fixation constructs that correspond to the specified data points or ranges clicked by the user within the plots.

The system may be capable of identifying candidates for optimal fixation constructs based on searching the results of the plurality of simulated designs or use of the surrogate models.

The individualized preoperative planning system may include a database for storing the design data of fixation designs, finite element models and surrogate models of designs. The database may be populated by running and saving computer simulations, before or during the preoperative planning process.

The fixation implant may be a plate fixated on a fractured bone with screws, an intramedullary nail, or other implant.

An individualized preoperative planning system may be configured to include the plate length, fracture gap size, number of the screws, positions of the screws and plate material as design input data.

An individualized preoperative planning system in accordance with the present invention may be configured to provide the biomechanics output including maximum stresses of the plate and the screws, stiffness of fracture fixation and strain at the fracture gap. Other related outputs include motions, predicted hardware fatigue life, predicted healing, and predicted hardware and surgical costs.

An individualized preoperative planning system in accordance with the present invention may be configured to develop the response surface model for each biomechanics output.

An individualized preoperative planning system in accordance with the present invention may provide visual data such as rotatable 3D images of fracture, 3D model manipulation, 3D plots superposed on 3D model, static or animated, and multivariate data plotting including but not limited to numeric, 2D & 3D plots of outputs vs. inputs, glyph, histogram, scatter matrix, brushing, parallel coordinates plots, etc. For example, an interactive parallel coordinates plot allows plotting of some or all of the design variables defining the fracture fixation construct design, and biomechanical outputs together. This plot also enables the user to select ranges of acceptable values for specific variables and narrow down the possible designs in order to identify optimal treatment.

In addition to the designs of the constructs, the design parameters may also include parameters defining a custom designed implant.

BRIEF DESCRIPTION OF THE FIGURES

FIG. 3 is a sample listing of combinations of plate length, fracture gap, number of screws, and associated screw positions for creating fracture fixation designs used for subsequent FEA (finite element analysis) simulations and surrogate model fitting;

FIG. 7 is a table showing a number of regressors and the resulting $R^2$ fit for the full quadratic surrogate model and the various simplified surrogate models tested; the simplified surrogate model using the $R^2$-based selection (5%) method (shaded column) is illustrated in FIG. 8;

FIG. 8 is a table showing regression coefficients for the surrogate model using the $R^2$ value (5%); these coefficients combine to form linear equations as shown in FIG. 9 for predicting each respective output variable; units of variables are provided in FIG. 4 (E);

FIG. 9 is a table showing linear equations formed with the regression coefficients illustrated in FIG. 8;

DETAILED DESCRIPTION OF THE PREFERRED EMBODIMENTS

Overview of Method

Figure 1:
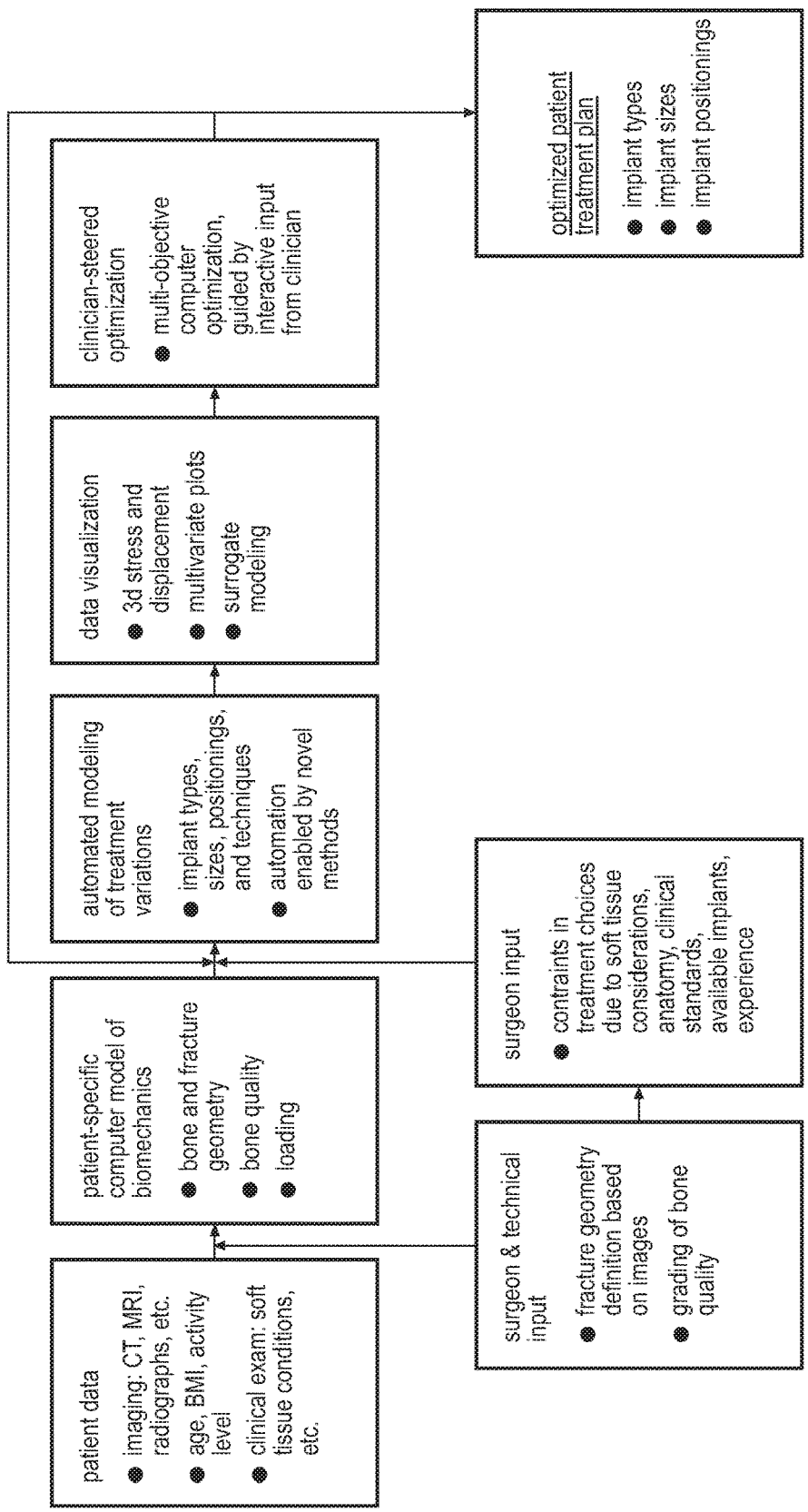
FIG. 1 is a flowchart showing a method for providing an individualized preoperative plan in accordance with the present invention.

The flow chart shown in FIG. 1 illustrates a novel method for providing an optimized and personalized patient treatment plan. First, an image-based 3D model is determined based on patient imaging data such as CT scans. MRI, and x-rays etc. of specific bone fractures. This model may be constructed during preoperative planning for a patient, or selected from a pre-existing database in order to adequately match the patient. Based on the bone and fracture geometry of this imaged-based model, 3D finite element models of the various fracture fixation designs can be constructed. The novel 3D finite element models utilize modularized blocks and simplified finite elements (such as beams used to represent screws) to perform computer experiments. Computer experiments refer to parametric variation of the inputs of a computer model to generate large numbers of designs. A novel model assembly approach is used to enable generation of hundreds of fracture fixation designs in an automated fashion. The fixation designs include variations in plate length, hardware material, screw locations, and fracture gap size.

Clinically important biomechanical outputs of the designs include but are not limited to maximum stress within the plates and screws, interfragmentary displacement, and construct stiffness.

The system requires interaction with the surgeon. The surgeon places constraints on the design variables based on soft tissue damage present in the patient, available implants, and experience. Furthermore determining optimal treatment involves simultaneously trying to optimize multiple objectives (e.g. reducing hardware stresses while providing adequate fracture gap strains), in which case the surgeon must evaluate tradeoffs between these objectives and make final treatment decisions. This is made possible by data visualization.

Figure 16A:
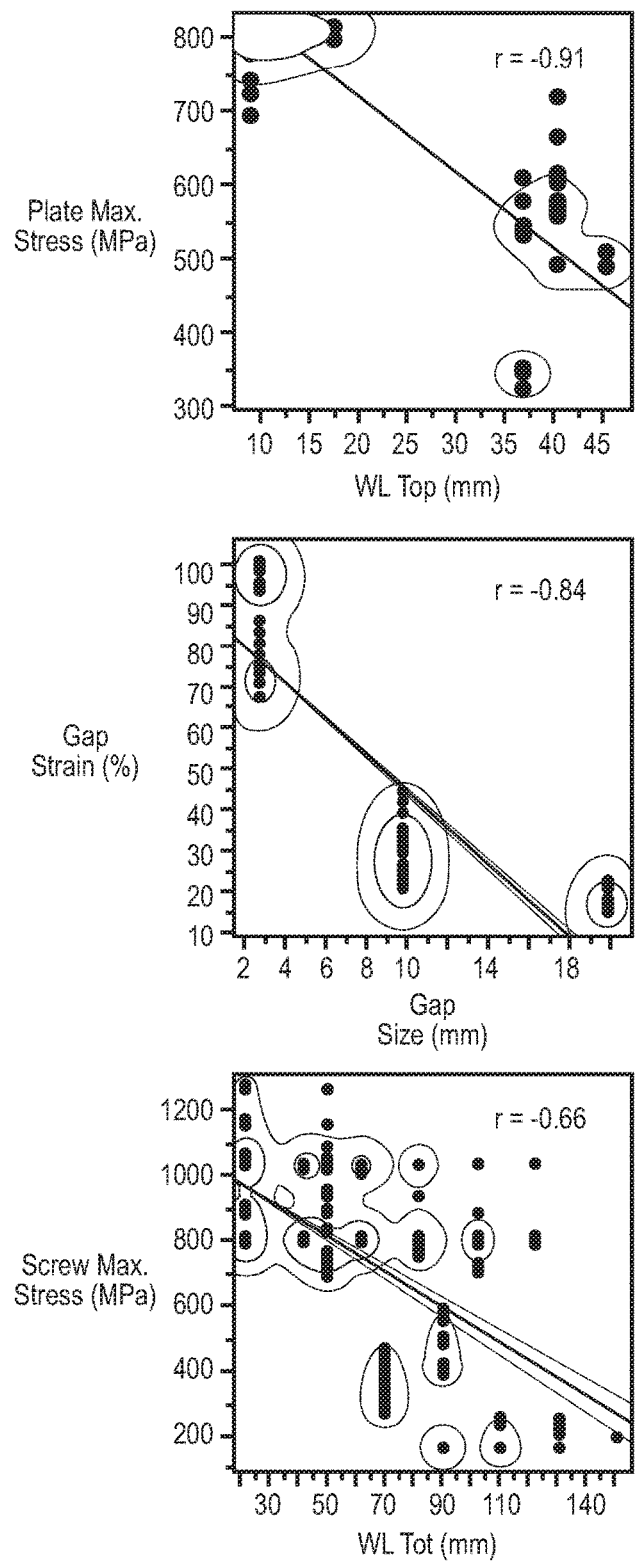
FIG. 16 is an illustration showing an example of a pairwise correlation analysis between design variables and biomechanics output.

Data visualization may be realized using significant pairwise correlation analysis between design parameters and the biomechanics outputs, as illustrated in FIG. 16.

Figure 11:
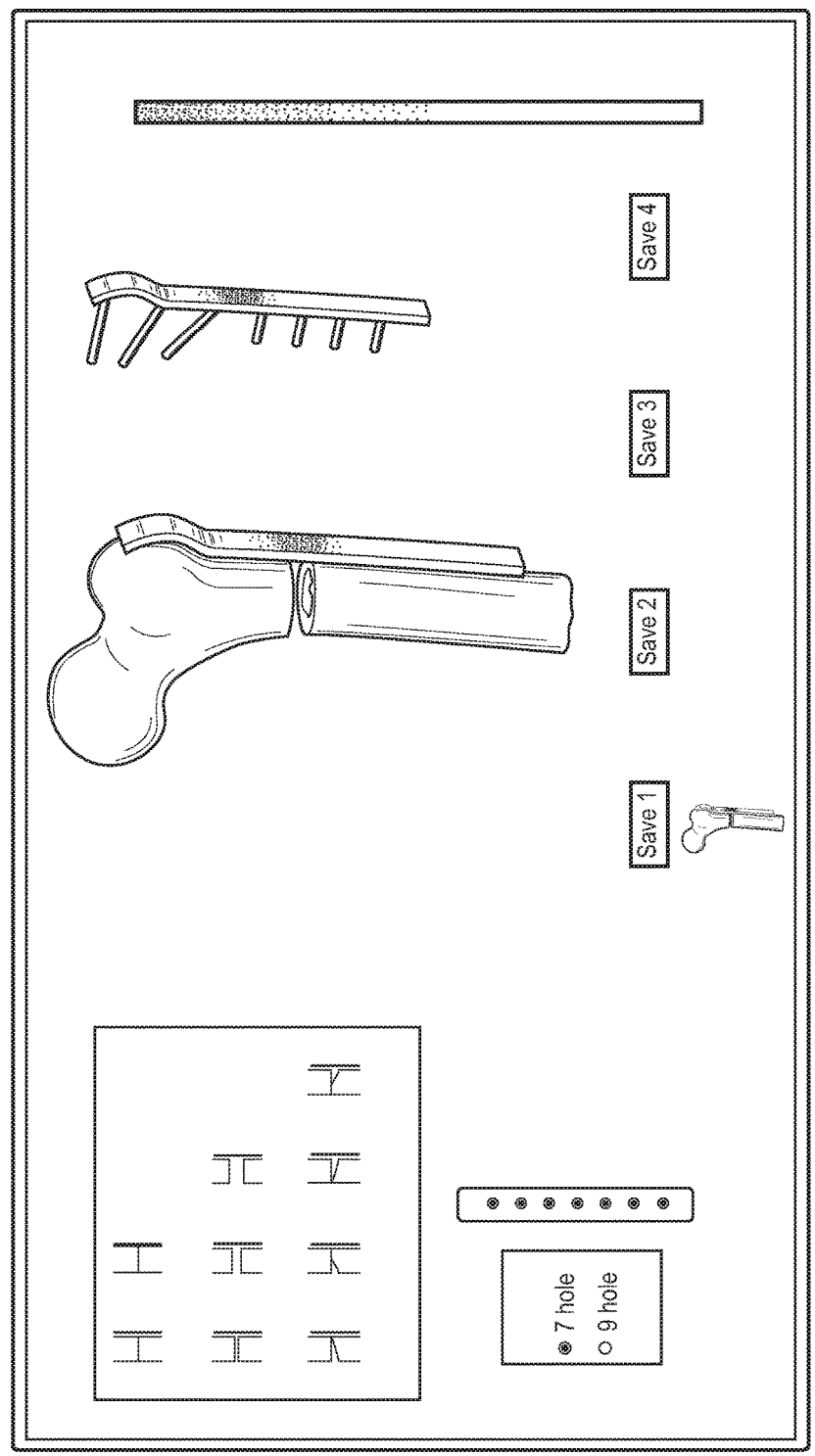
FIG. 11 is an illustration showing an embodiment of a graphical user interface for femur fracture fixation in accordance with the present invention.
Figure 16B:
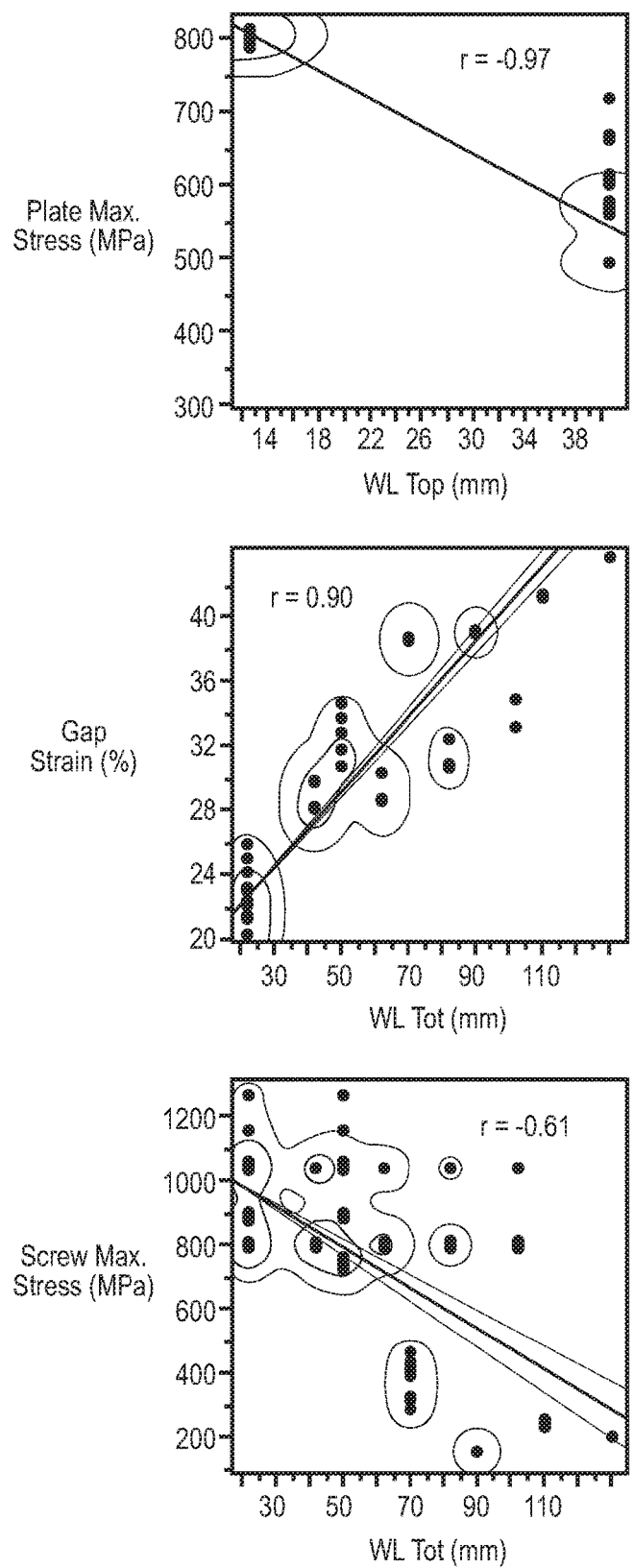

FIG. 16 (A) shows all unsupported fracture types (3, 10, and 20 mm) for the femur fixation modeling also displayed in FIG. 11 with 500 N load (n=664). FIG. 16 (B) shows 10 mm fracture gap and 500 N load (n=272). Black dots indicate FE result, and colors indicate data density. In unsupported fracture types, the most influential variables in determining plate maximum stress and screw maximum stress are total working length $WL_{tot}$ and top working length $WL_{top}$. Gap size was highly influential on gap strain as expected. For the 10 mm gap unsupported fracture type, the gap strain was increased with the increase of $Va_{tot}$ as shown in FIG. 16(B).

Figure 15A:
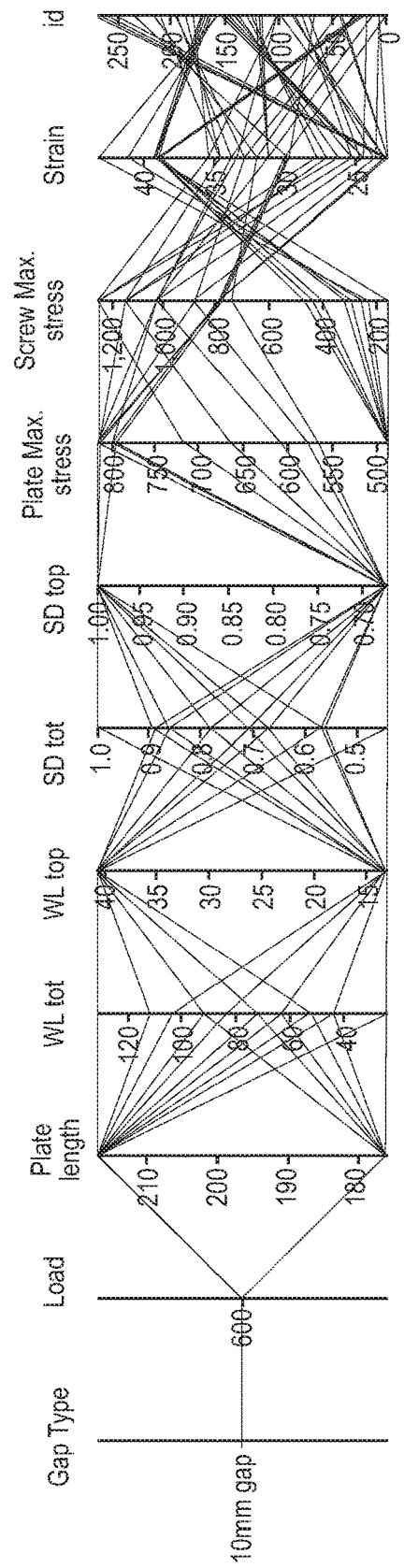
FIG. 15 is an illustration showing an example of an interactive parallel coordinate plotting.
Figure 15B:
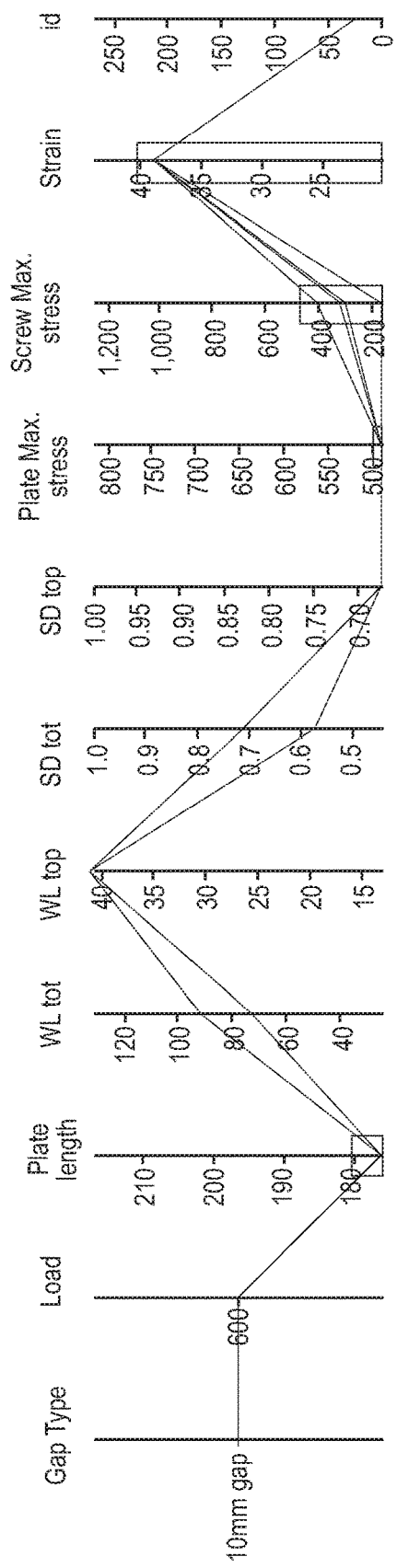

Data visualization may be realized using multivariate plots such as parallel coordinates plots, as shown in FIG. 15. FIG. 15 shows interactive parallel coordinate plotting based on the femur fixation modeling also displayed in FIG. 11. Each connected polyline represents a single fracture fixation construct. (A) is a plot for all fracture fixation constructs with 10 mm gap unsupported fracture type and 500 N load (n=272). In (B), optimal constructs (n=4) were identified by limiting (red highlight) to the smaller plate length, maximum plate and screw stresses below endurance limit of 450 MPa for 316L SS, and fracture gap strain below 40%.

Multivariate data plot allow plotting of all the design and output variables together for all possible treatments. The surgeon can interact with the plots by selecting acceptable ranges for certain variables and view the corresponding fracture fixation construct designs. The surgeon can narrow down the treatments and look for patterns to inform treatment.

Data visualization may also be realized based on the surrogate models. These statistical response surfaces such as the one shown in FIG. 10 can offer (1) insights into which input parameters have a large effect on the output and which do not; (2) prediction of output for a new combination of inputs; and (3) design optimization to determine the best combination of inputs.

In addition to data visualization, a user may interact with the data using a graphical interface. A user may be presented with fracture cases and may create a series of fracture repair constructs. Upon each adjustment of the construct, the resulting 3D stresses and strains across the fracture site and implant will be immediately displayed. Success or failure in achieving certain biomechanical criteria will be displayed. Surgeons can rely on these feedbacks and combine with clinical standards and their own experience to optimize an individualized patient treatment plan.

Overview of an Individualized Treatment Planning, System

Figure 2:
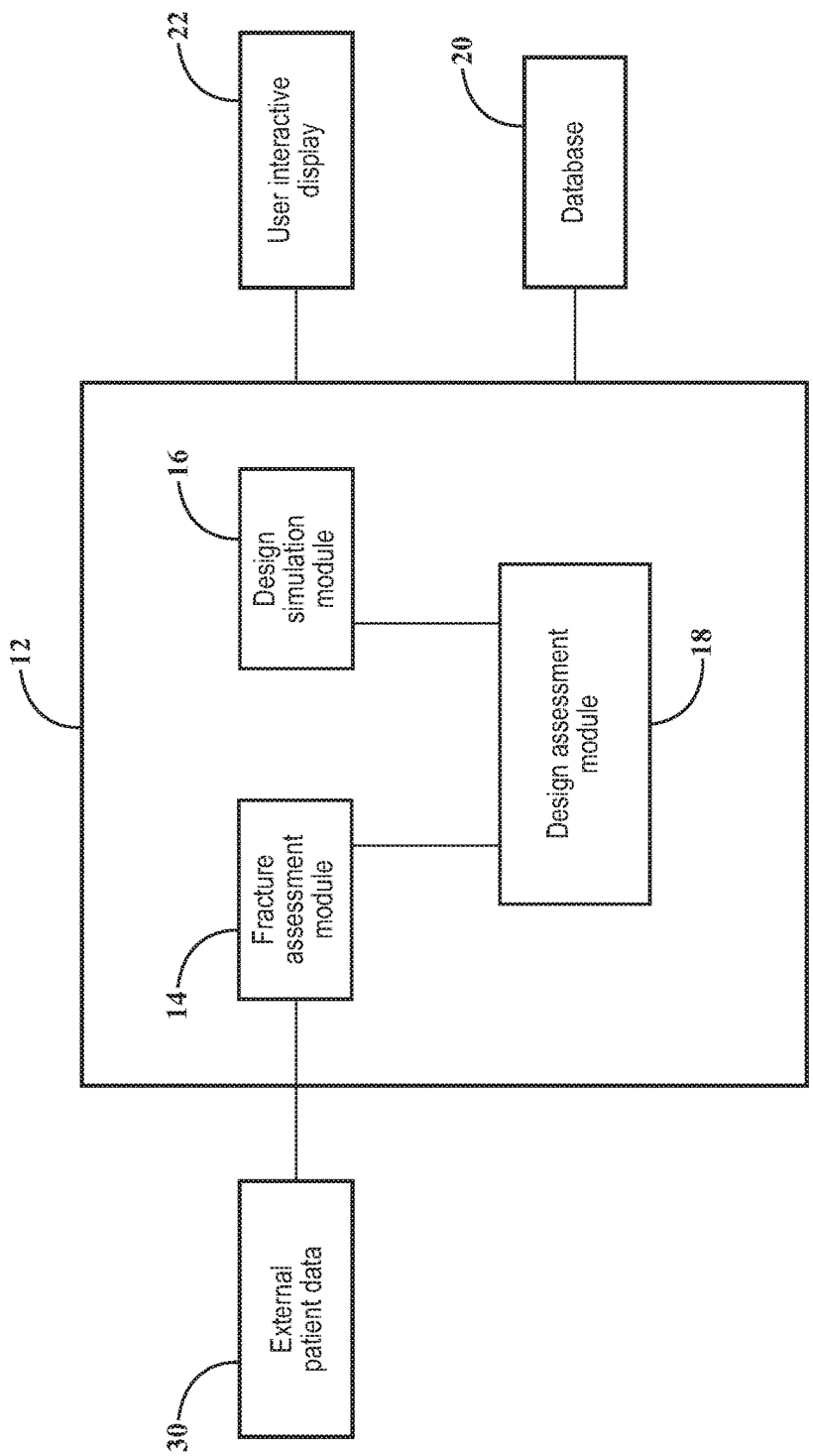
FIG. 2 is a block diagram of an embodiment of an individualized treatment planning system in accordance with the present invention.
Figure 4B:
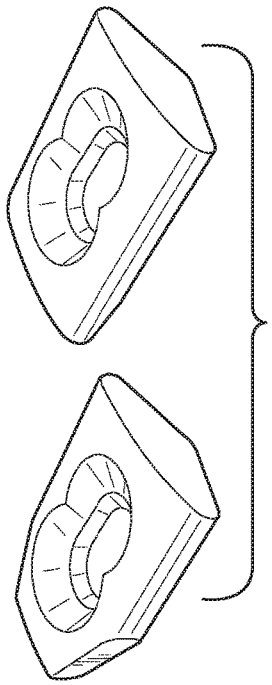
FIG. 4 is a view of modular components used to build finite element models of the fracture fixation construct, design variables of the fracture fixation construct design and an example of the fracture fixation construct design.
Figure 4F:
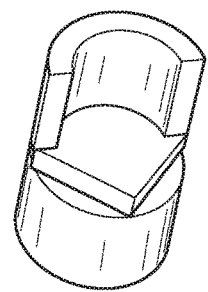
Figure 4A:
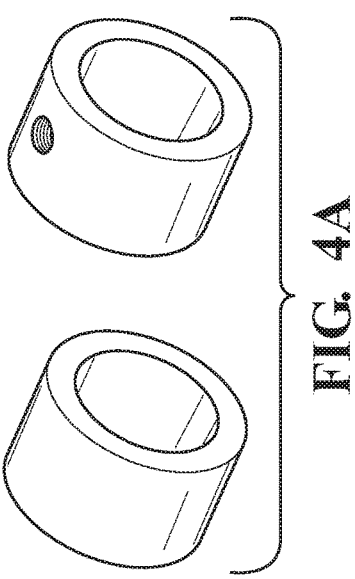
Figure 4C:
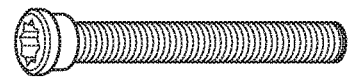
Figure 4D:
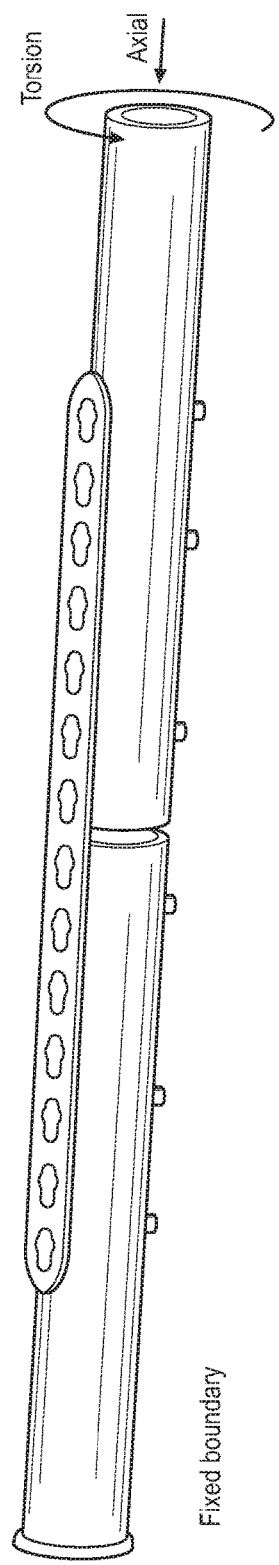
Figure 4E:
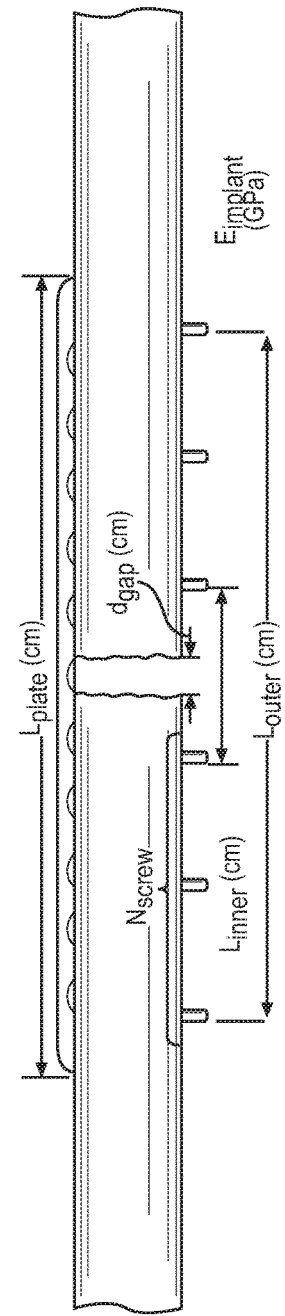

FIG. 2 illustrates a block diagram of an individualized treatment planning system. The processing unit 12 includes a fracture assessment module 14, a design simulation module 16 and a design assessment module 18. The external patient data 30 is received by the fracture assessment module 14 for analysis. The external patient data 30 includes but is not limited to imaging data such as CT scans, MRI, and x-rays etc. of a patient's specific bone fractures. The fracture assessment module 14 utilizes a model to evaluate the fracture fixation. This model may be a 3D finite element model. This model may be constructed during preoperative planning for a patient, or selected from a pre-existing database in order to adequately match the patient. A corresponding appropriate fracture fixation implant and construct is then recommended. Within the design simulation module 16, a large number of finite element model simulations of all possible designs are performed ahead of time with a range of different values for fracture types, fracture sizes and fixation construct design parameters. The results of the simulations are saved in the database 20 and can be retrieved by the design assessment module 18. The results include the design parameters and the biomechanics performance of the designs. The design assessment module can utilize these results in a number of ways. These results can be used to generate 2D, 3D or multivariate plots depicting the relationship between the design parameters and biomechanics outputs. The large number of results can also be used to develop a surrogate model.

Within the design simulation module 16, a surrogate model or response surface can be generated for each biomechanical criteria that gives an estimate of each biomechanical criteria as a function of the fracture type, fracture size and fixation implant design parameters using the large number of finite element model simulation results.

A surgeon can manipulate the design parameters through the user interactive display 22. The design assessment module 18 receives the design parameters input from the user interactive display 22 and communicates to the design simulation module 16. The biomechanics corresponding to the user design input is then computed based on the surrogate model and then sent back to the user interactive display 22 for the surgeon to view. The surgeon can view the results and compare with the value of each biomechanical criteria that is optimal for the patient healing and decide whether it is necessary to modify the design accordingly.

The user interactive display 22 may also be an interactive plot such as a multivariate plot, e.g., a parallel coordinates plot. On these plots, the surgeon can select points or ranges of design parameters or biomechanics outputs and the design assessment module will enable the surgeon to view the corresponding fracture fixation construct design and help the surgeon to narrow down the designs for optimal treatments.

Interactive Human-Computer Interfaces

Interactive human-computer interfaces enable physicians, researchers and students to visualize biomechanics and manipulate it through design. The system allows users to select and modify the fixation design parameters such as the implant shape, number of screws and positions of the screws. FIG. 11 shows an embodiment of the interactive graphic interface for the individualized preoperative planning system. Via this interface, users can select the fracture gap size and number of screws. Then the system will present the user with a rotatable 3D image of the locking plate fixated on the fracture site. The user, usually a surgeon, will create a series of fracture repair constructs. Upon each adjustment of the construct, the resulting 3D stresses and strains across the fracture site and implant will be immediately animatedly displayed. This visualization is a high fidelity improvement over what many surgeons often attempt within their minds during preoperative planning but typically can only crudely approximate (at best) especially in more complex cases. The immediate update is made possible because the finite element model simulations of all possible fixation designs have been previously computed with results stored in a database that can be quickly retrieved by the system. In this example shown in FIG. 11, two types of plates may be selected, a 7-hole plate or a 9-hole plate. A fracture type and fixation type may be selected through this interface. Various fracture and fixation types include simple transverse without compression, simple transverse with compression, transverse with 3 mm gap, transverse with 10 mm gap, transverse with 20 mm gap, oblique with medial point contact, oblique with medial half contact, oblique with lateral point contact and oblique with lateral half contact. Animate loading may be done through this interface. Fracture fixation designed may be saved. The interface displays 3D deformed bodies (bones) and 3D field plots based on the selected fracture type and design type.

Figure 12:
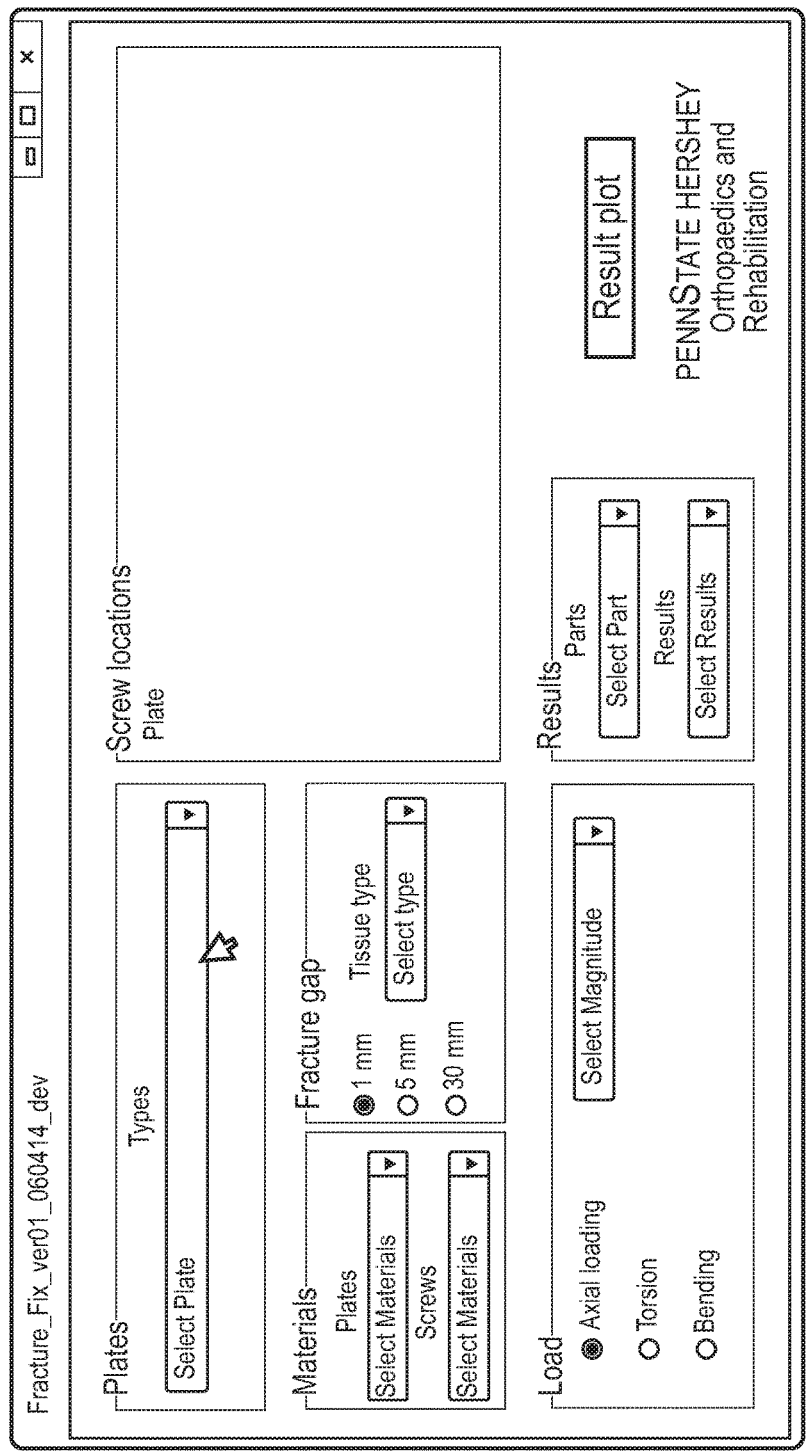
FIG. 12 is an illustration showing a snapshot of an embodiment of an interactive computer interface for training in accordance with the present invention.
Figure 13:
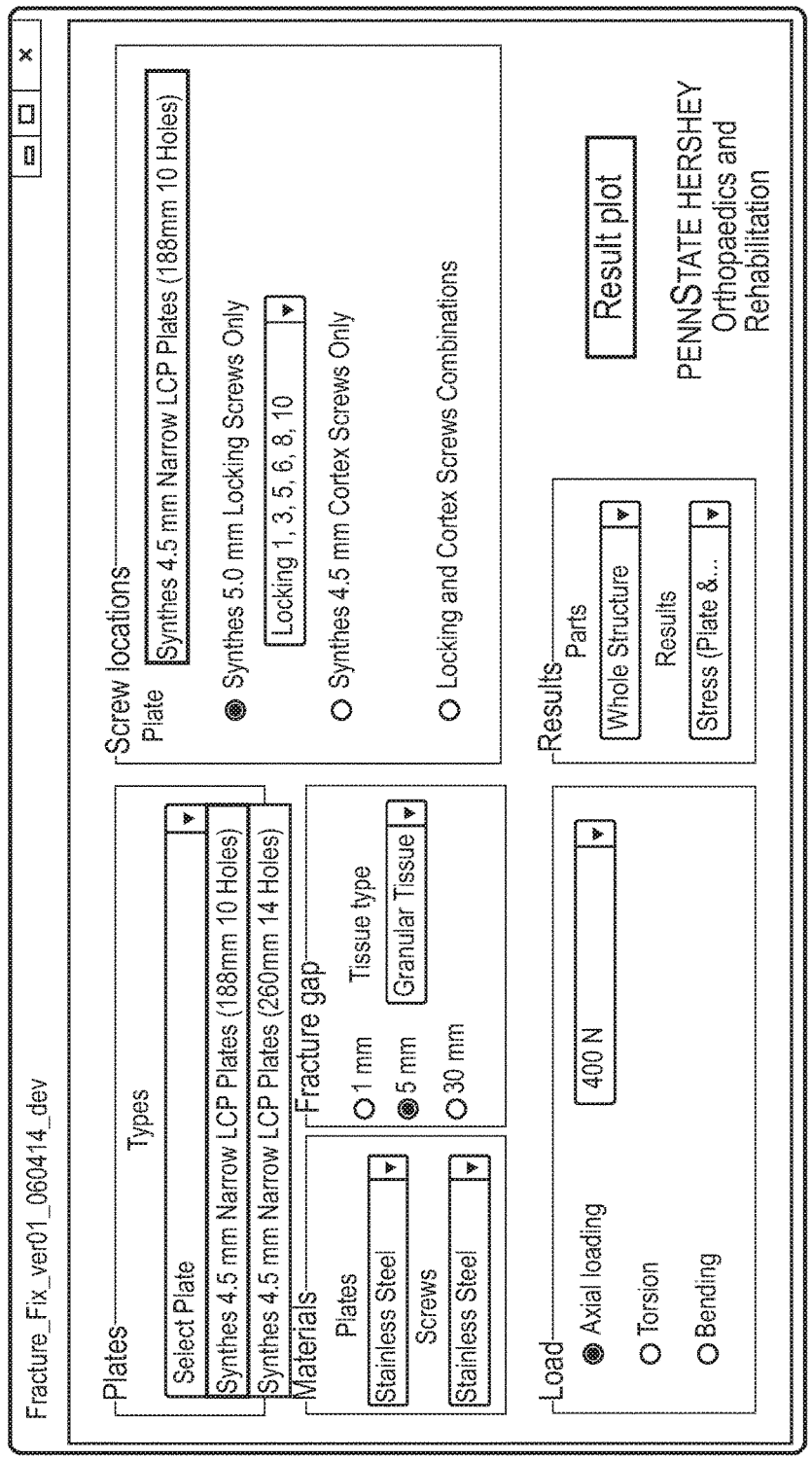
FIG. 13 is an illustration showing another snapshot of an embodiment of graphical user interface for training in accordance with the present invention.
Figure 14:
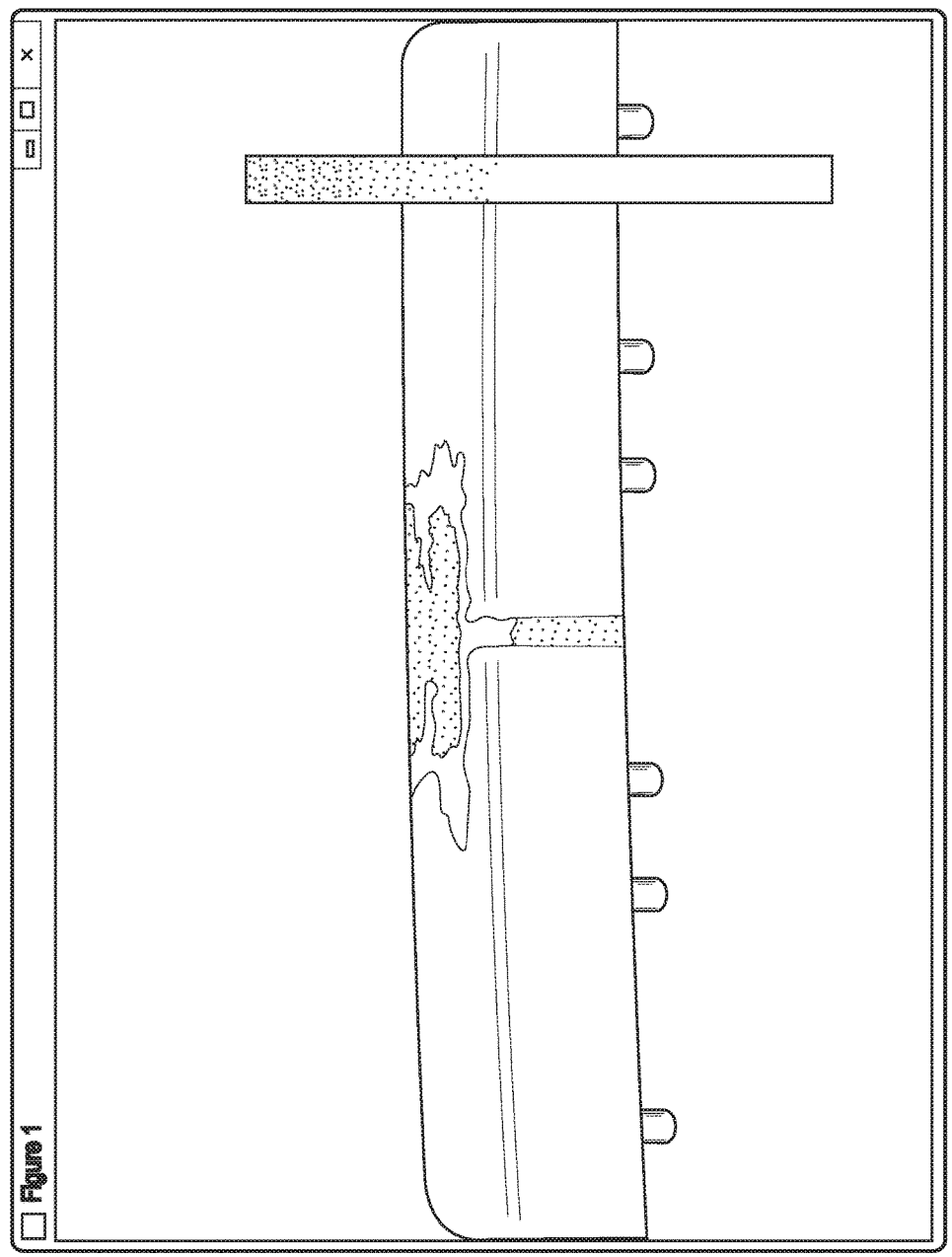
FIG. 14 is an illustration showing an example of a resulting plot generated from the graphical interface shown in FIGS. 12 and 13.

FIG. 12 shows an interactive computer interface for training purposes. FIG. 12 illustrates a snapshot of the interface before any selection is made. On this interface, a user may select the type of plate which indicates the length of the plate and the number of holes in the plate; the material of the plate; the fracture gap size; the tissue type, the type and magnitude of the load on the bone; the screw locations; and the type of display for the results to be displayed. In FIG. 13, the same interface is shown but the exemplary selections have been made. FIG. 14 shows an example of the visual feedback related to a particular design available for the physicians to view.

FIG. 15 shows an example multivariate data plot that allows plotting all the design and output variables together for all possible treatments. The surgeon can look for patterns to inform treatment, and/or select acceptable ranges for certain variables and narrow down the treatments which meet these criteria. This and other multi- and univariate plotting capabilities (e.g. FIG. 10) are being integrated into the interfaces shown in FIGS. 11 & 12 so that the user can interact with the biomechanics data in multiple ways.

Detailed Description of Method a. Finite Element Model Cases

Figure 5A:
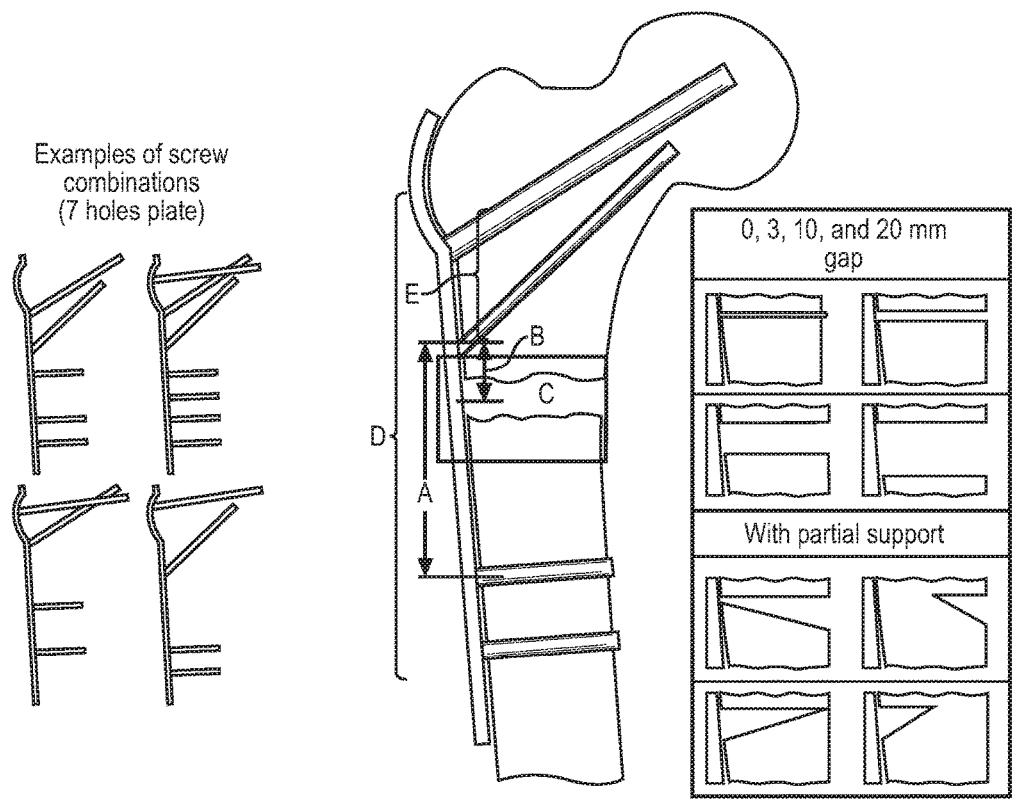
FIG. 5 is a schematic showing an example of an FE (finite element) model of subtrochantreric femur fracture fixation with a lateral plate and screws into the bone; (A) design variables defining the fracture pattern and surgical fixation are shown; (B) loading and boundary conditions are shown.
Figure 5B:
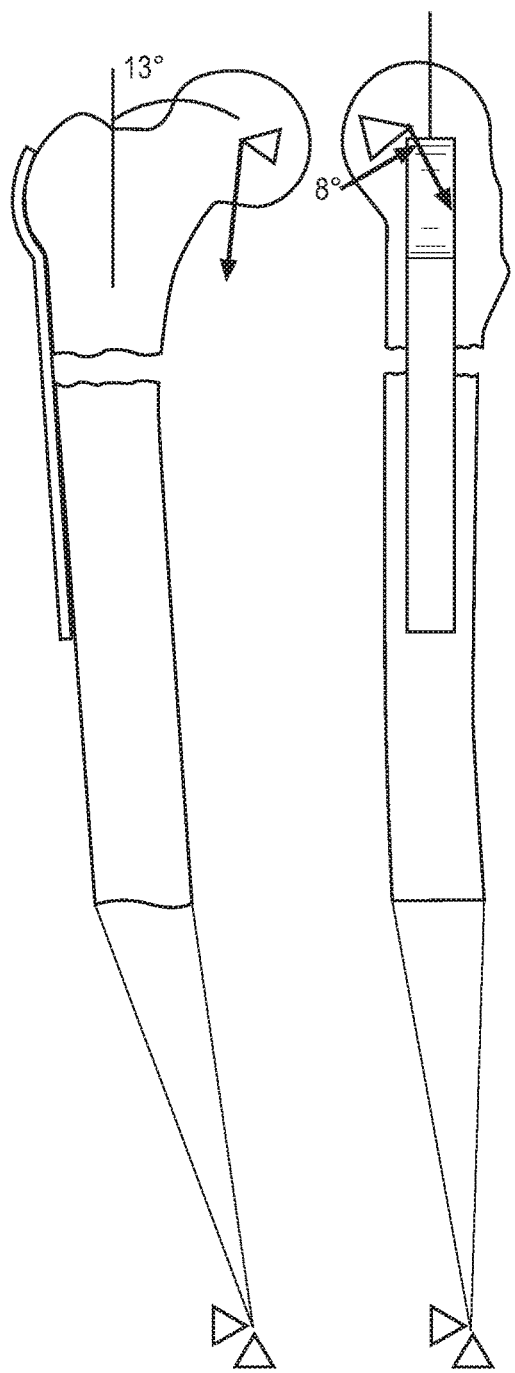
Figure 6A:
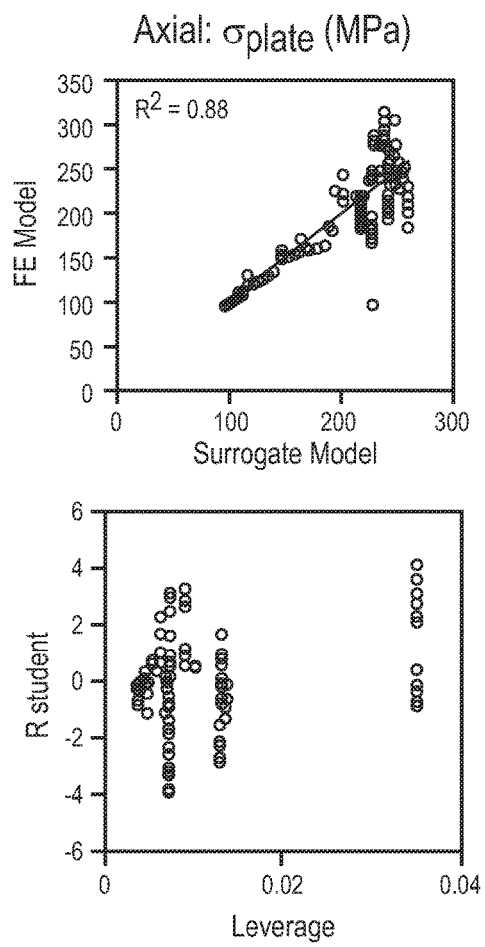
FIG. 6 provides scatter plots showing example fits between surrogate statistical model-predicted values and FE model "observed" values that are used to fit the surrogate model (top row); the bottom row shows plots of leverage vs. R-Student for the same models.
Figure 6B:
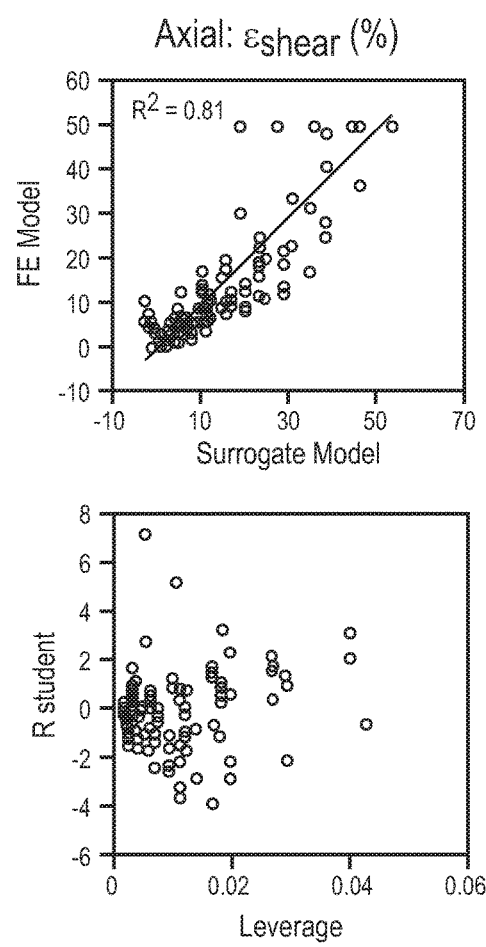
Figure 6C:
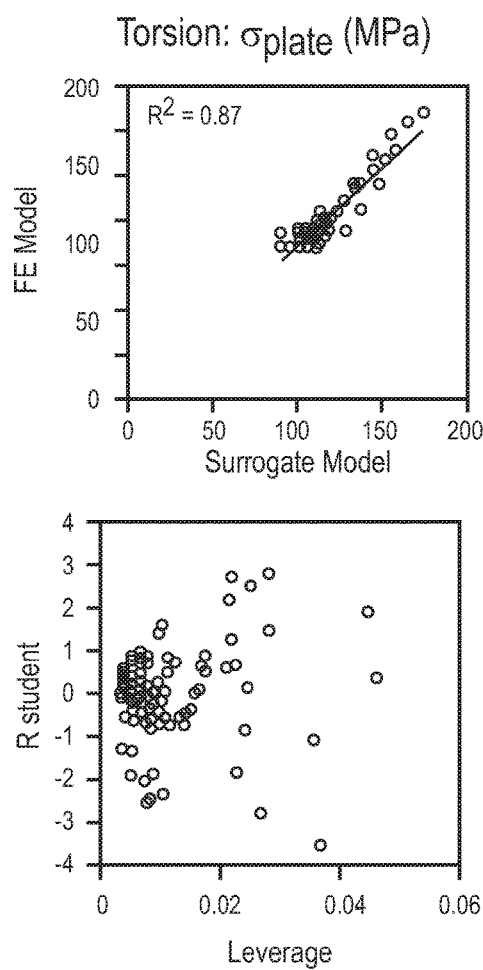
Figure 6D:
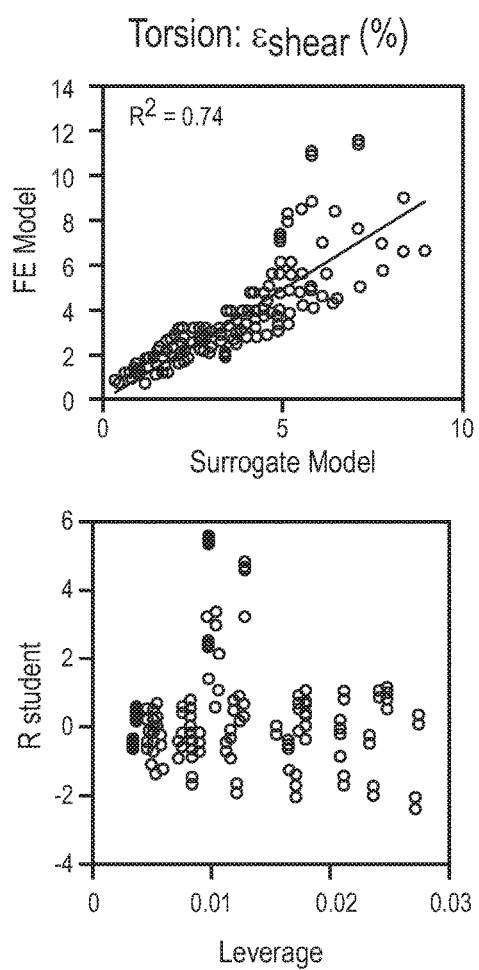
Figure 10A:
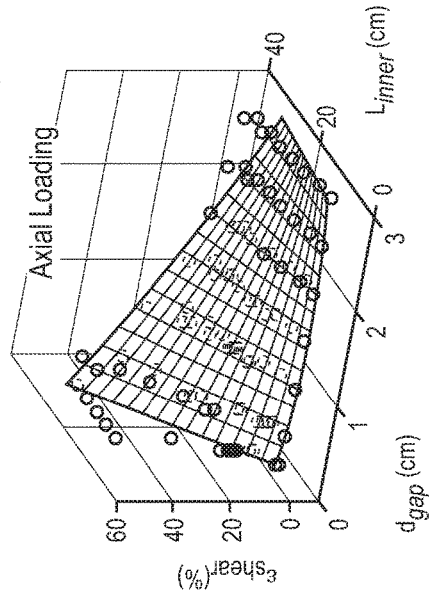
FIG. 10 provides plots showing response surfaces based on the $R^2$-based selection simplified surrogate models reported in FIG. 7; the dots are the FEA results used to fit the surrogate models; (A) and (C) illustrate the stiffness of the fracture fixation construct response surface as a function of $L_{inner}$ and $E_{implant}$; (B) and (I)) illustrate the shear strain response surface as a function of $d_{gap}$ and $L_{inner}$.
Figure 10B:
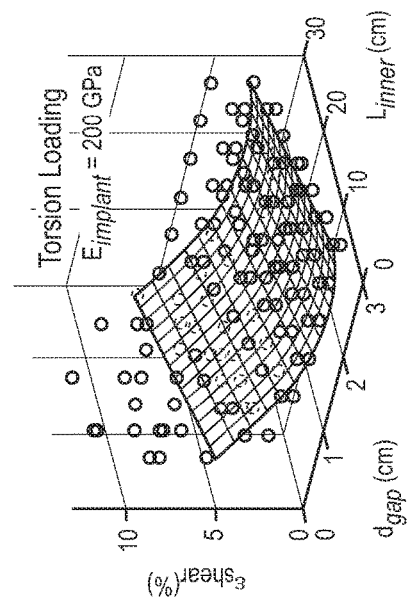
Figure 10C:
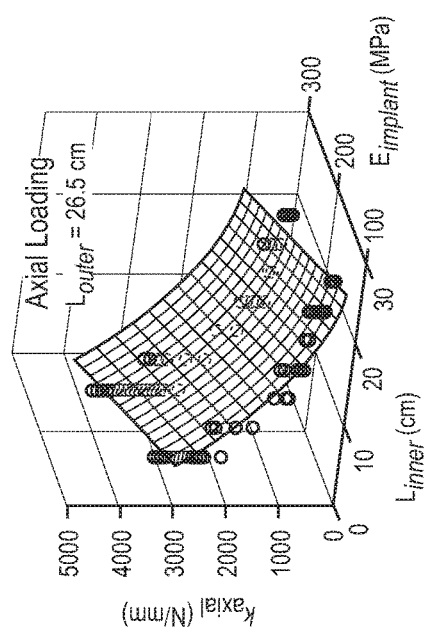
Figure 10D:
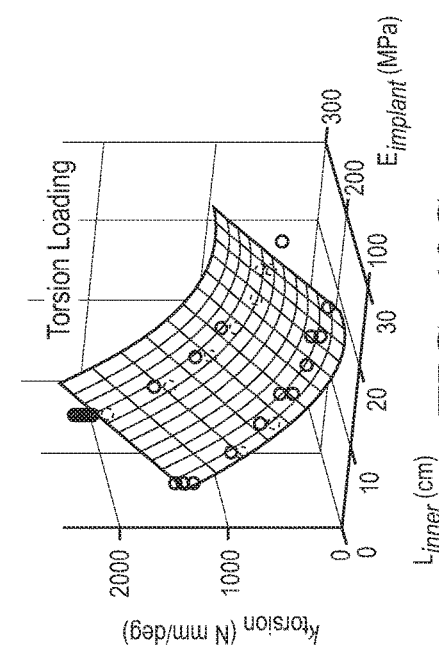

FIG. 5 shows an example of a finite element model of a subtrochantreric femur fracture fixation with a lateral plate and screws into the bone. The fracture pattern is defined by the fracture gap size and whether the fracture is with or without partial contact. Fracture fixation is defined by the total working length (or outer working length) of the plate, the top working length (or the inner working length) of the plate, the number of screws and the positions of the screws. Generic plates are 176 (7-hole) and 217 (9-hole) mm length. Screws are 7.3 mm diameter cannulated locking screw and 5.0 mm diameter solid locking screw. Screw density is the number of screws/number of total possible screws.

As a simple representative case of locked plated fracture fixation, diaphyseal midshaft fracture fixation is modeled such as would occur in the treatment of a midshaft femur, tibia, or humerus fracture (FIGS. 3 & 4). FIG. 3 shows an example listing of combinations of plate length, fracture gap, number of screws, and associated screw positions for creating fracture fixation designs used for subsequent FEA simulations and surrogate model fitting. A total of 774 fracture fixation designs were modeled in this example. The long bone was modeled with a hollow cylinder for cortical bone (30 mm outer diameter and 4.3 mm cortical thickness). Fractures were simulated with simple transverse cuts, and seven cases for fracture gap sizes were considered ($d_{gap}$=2, 5, 10, 15, 20, 25, and 30 mm). Five lengths of plate (4.5 mm Narrow Locking Compression Plate, Depuy Synthes) were modeled: $L_{plate}$(hole#)=15.2 cm (8), 18.8 cm (10), 22.4 cm (12), 26 cm (14) and 29.6 cm (16) holes plate, and locking screws were modeled (5 mm diameter, Synthes). Additional model input variables that are varied include screw configuration, implant materials (stainless steel and titanium alloy), and loading type (axial and torsion). For automatic creation of all fixation designs, modularized finite element models for bone, plate and screw are created using Abaqus (ver 6.13-2, Dassault, Providence, R.I.) and assembled using custom-written code in Matlab (ver14, Mathworks, Natick, Mass.). FIG. 4 shows modular components used to build full models. FIG. 4(A) shows bones with or without a screw hole. FIG. 4(B) shows locking plate parts. FIG. 4(C) shows a locking screw. FIG. 4(F) shows a virtual 8-node hexahedral element at the fracture gap used to compute maximum shear strain in that region. FIG. 4(E) shows design variables of fracture fixation designs which serve as regressors in the response surface statistical models. FIG. 4(D) shows an example of a fracture fixation design achieved by automated assembly of the bone, plate, and screw parts, in this case with a 5 mm fracture gap, 14 hole plate, and screws positioned at holes 1, 3, and 6.

b. Finite Elements Quadratic tetrahedral elements are utilized for the plate model which is meshed from manufacturer-supplied CAD files, and hexahedral elements are used to model the bone and screws. Mesh convergence testing is performed using a range from 80,000 to 1,401,000 total elements. Using approximately 100,000 elements, results (gap displacement, construct stiffness, and maximum stress) converge with less than a 2-8% difference compared to the model with the largest number of elements.

c. Materials, Interactions and Constraints

A transversely isotropic linear elastic material model is used for the cortical bone (Ex=17 GPa, Ey=Ez=11.5 GPa, vxy=vx, =0.31, vyz=0.58, Gxy=Gx, =3.3 GPa, Gyz=3.6 GPa). Fracture fixation implants are modeled as linear isotropic materials (stainless steel: E=200 GPa, v=0.3 and titanium: E=110 GPa, v=0.3). Coulomb friction (µ=0.3) is assumed for the surface interaction between plate and bone. The surfaces between the thread of the locking screw head and plate are tied together, and the surface between the locking screw thread and bone hole are tied together. Axial compression loading of 400 N is applied to the proximal end of the bone to simulate postoperative toe-touching weight bearing, and the distal end of the long bone is rigidly fixed. For torsional loading, 2 Nm is applied to the proximal end of the long bone. In both loading cases, proximal end translations are constrained in directions perpendicular to the long axis of the bone.

d. Finite Element Model Outputs

Maximum von Mises stresses of the plate ($\sigma_{plate\_max}$) and screws ($\sigma_{screw\_max}$) are determined. Stresses at the interfaces between the screw heads and the plate holes are ignored because of difficulty in accurately modeling these threaded interfaces, and because these interfaces do not tend to fail clinically. The stiffness of the fracture fixation construct ($k_{axial}$ and $k_{torsion}$) is computed as the ratio of applied load (axial or torsional) to proximal bone displacement (axial or rotational). In order to determine interfragmentary strain at the fracture gap, a virtual 8-node hexahedral element connecting the two bone ends at the fracture gap is utilized (FIG. 4(E)). The deformation gradient of the virtual hexahedral element is calculated by the shape function based on nodal displacements. The Green strain tensor is then obtained from the deformation gradient. Maximum shear strain at the fracture gap ($\varepsilon_{shear}$) is calculated from the maximum and minimum principal strains.

e. Full Quadratic Regression Models

Polynomial regression models, or response surfaces, are developed for each model output separately with the statistical software SAS (Release 9.3, SAS Institute Inc., Cary, N.C.). The regressor variables are defined based on the modeling inputs and included plate length ($L_{plate}$), fracture gap size ($d_{gap}$), number of screws ($N_{screw}$), screw working lengths between inner screws ($L_{inner}$), and between outer screws ($L_{outer}$), and hardware material elastic modulus ($E_{implant}$). Linear, quadratic, and interaction forms of the regressors (a total of 26) are included in the full models: six linear regressor variables, 5 quadratic regressor variables, and 15 interactive regressor variables. The biomechanical results of $\sigma_{plate\_max}$ and $\sigma_{screw\_max}$, construct stiffness ($k_{axial}$ and $k_{torsion}$), and octahedral shear strain of fracture gap ($\varepsilon_{shear}$) are defined as response variables.

f. Simplified Regression Models

Because full quadratic models (26 regressors) are complex and can be challenging to interpret, simplified models with a smaller number of the more influential regressors are also fit. Six different approaches for simplified regression models are tested, in which new models are fit (treating each response variable separately):

(1) Full quadratic: using all 26 regressors as defined in previous section;

(2) Significant regressors: using the subset of regressors that are statistically significant (p<0.05) from the hall quadratic model;

(3) $R^2$-based selection (1%): a model with the least number of regressors which produced an $R^2$ value less than 1% different than that of the full quadratic model (RSQUARE method in SAS was used to test all possible combinations of regressors;

(4) $R^2$-based selection (5%): a model with the least number of regressors which produces an $R^2$ value less than 5% different than that of the full polynomial model;

(5) Stepwise selection: a stepwise addition and elimination approach, in which various combinations of regressors are tested, and variables are added one by one to the model with the significance of 15%, and then any variable that is not significant (5%) among the variables included in the model are deleted; and (6) Linear regressors: a simple linear model that only includes the 6 linear regressors, without any quadratic or interaction terms.

g. Experimental Validation

Polyvinyl chloride (PVC) tubing (33.4 mm outer diameter and 4.5 mm wall thickness) with a 400 mm length is used to represent bone. Simple transverse cuts are made to simulate the fracture, and three fracture gaps (2, 10, and 20 mm) are used. Two lengths of plates (4.5 mm Narrow LCP plate, 10 (18.8 cm) and 14 (26 cm) holes plate, Synthes) and 5 mm diameter locking screws (Synthes) are used for fixation, and nine screw configurations for each plate are tested. Similar constraints and loadings are applied to the experimental setup as described above for the finite element model. Axial or torsion loading is applied with a dual actuator servo-hydraulic test machine (Interlaken 3300 with Flex test 40 controller, MTS, Eden Prairie Minn.). Actuator force or torque are measured by in-line load cells (axial force: 500 lbf capacity, Interface, Scottsdale, Ariz., torsion, torque; 45 Nm capacity, Omegadyne, Sunbury, Ohio). The recorded actuator displacement or rotation, and force or torque, are used to calculate structural stiffnesses, and the interfragmentary motion is measured at the cortex opposite the plate with a digital caliper with a 0.01 mm resolution and 0.02 mm accuracy (TruePower 6 inch digital caliper, Simi Valley, Calif.).

Results a. Finite Element Model Outputs

Maximum von Mises stresses of the plate average 156 MPa (range 94 to 314 MPa) and 114 MPa. (range 97 to 184 MPa) across the 774 simulations for axial and torsion loading, respectively. In axial loading, these maximum stresses generally occur at the surrounding bottom surface of the unlocked screw hole next to the applied locked screw that is close to the fracture gap in the proximal part of the fracture segment while maximum stress of torsion loading are generally located at the top surface of the plate holes between two screws close to the fracture cap. Maximum stresses in the screws average 85 MPa (range 40 to 263) for axial loading and 104 MPa (range 72 to 185) for torsion loading. These maximums generally occur at the screw thread close to the interface between the bone and screw; it is located at the distal surface of the screw close to the fracture gap in axial loading and the lateral or medial surface of screws close to the fracture gap. The stiffness of the fracture fixation construct averages 2397 N/mm (range 421 to 4095) for axial loading, and 1405 N mm/° (range 316 to 2255). Maximum shear strain at the fracture gap averages 6.12% (range 0.03 to 324.21) for axial loading and 2.33% (0.75 to 11.63) for torsion loading.

The location of the maximum von Mises stress in the plate appear to vary, qualitatively, with $L_{inner}$ (FIG. 5). An increase of $\sigma_{plate\_max}$ is observed in these plots when the inner working length was increased, with the number of screws held constant. An increase in fracture gap size does not appear to substantially affect the stress distribution in the plate. Higher stress concentration is observed at the surrounding unlocking screw holes. With changes in the number of screws (Nscrew 2, (1,5) and $N_{screw}$=3, (1,3,5)), if the inner working length is the same, the plate stress distribution shows a very similar pattern. When considering the same configuration of screws, an increase of $d_{gap}$ caused the decrease of $\varepsilon_{shear}$ at the fracture gap.

b. Full Quadratic Regression Models

The full quadratic models with 26 regressors, fit for each output variable, show good fitting between the surrogate model values and FEA results with the $R^2$ values from 0.84 to 0.99 and 0.88 to 0.99 for axial and torsion loading, respectively (FIG. 7).

c. Simplified Regression Models

Using the Significant regressors method, the number of regressors is reduced to less than half of that in the full quadratic models, without substantial loss in model fitting with $R^2$ ranging from 0.81 to 0.98 and from 0.74 to 0.99 for axial and torsion loading, respectively (FIG. 7). In general the construct stiffness output variables are modeled best by these simplified surrogate models, and maximum shear strains are fit the worst.

Using the $R^2$-based selection (1%) method, the number of regressors ranges from 5 to 6 (the $R^2$ ranging from 0.83 to 0.98) for axial loading, and from 5 to 9 (the $R^2$ ranging from 0.76 to 0.99) (FIG. 7). Using the $R^2$-based selection (5%) method, the number of regressors is further reduced to a range of 3 to 4, and 3 to 7 for axial and torsion loading respectively (FIG. 7), with some concomitant loss in model fitting, with $R^2$ ranging from 0.81 to 0.97 and 0.74 to 0.96 for axial and torsion loading respectively.

Using the Stepwise selection method, the number of regressors ranges from 6 to 12 with ranging from 0.83 to 0.99 for axial loading, and the number of regressors ranges from 10 to 15 with $R^2$ ranging from 0.76 to 0.99 for torsion loading. Using the linear regressors method, $\sigma_{plate\_max}$ in axial loading and construct stiffness in both loadings are fit well, although with resulting $R^2$ values less than that when using the $R^2$-based selection (5%) method.

d. Simplified Regression Models: Focus on $R^2$-Based Selection (5%) Method

Using the $R^2$-based selection (5%) method, the estimated linear coefficients for each regressor are provided in FIG. 8. All these regression coefficients are statistically significant (p<0.0001). The residuals between the regression model-predictions and FEA results show an increase with an increase of plate stress and shear strain (for axial loading), and with an increase in maximum shear strain (for torsion loading) (FIG. 6). Moreover, some influential and outlying observations are observed in the plot of R-Student by leverage values. Leverage of all response in both loading shows in similar cases. For $\sigma_{plate\_max}$, $k_{axial}$, $\varepsilon_{shear}$, the longest $L_{plate}$ with the least $N_{screw}$ and the longest $L_{inner}$ show a large leverage in both loading conditions. For $\sigma_{screw\_max}$, the longest $L_{plate}$ with the highest $N_{screw}$ and the shortest $L_{inner}$, show large leverage in axial loading case while the longest $L_{plate}$ with the least $N_{screw}$ and the longest $L_{inner}$, show large leverage in torsion loading.

Writing out the fit polynomial models, for example, the predicted response of maximum plate stress and shear strain are shown in FIG. 9.

For example, if $L_{outer}$ is 23 cm, $E_{implant}$ is 200 GPa, and $d_{gap}$ is 1 cm, when $L_{inner}$ is increased from 5 cm to 20 cm, the predicted increase in $\sigma_{plate\_max}$ under axial loading will be around 56% (from 110 to 250 MPa). In a similar way, if $L_{inner}$ is 10 cm, and $E_{implant}$ is 200 GPa, and when $d_{gap}$ is increased from 0.2 to 1 cm, $\varepsilon_{shear}$ will be decreased by 80% (from 13.5 to 7.5%).

The response surfaces can be written with function forms; in axial loading, $\sigma_{plate\_max}=g(L_{inner}, E_{implant}, L_{out})$, $\sigma_{screw\_max}=g(L_{inner}, N_{screw})$, $k_{axial}=g(L_{inner}, E_{implant}, L_{out})$, and $\varepsilon_{shear}=g(L_{inner}, d_{gap})$, and for torsion, $\sigma_{plate\_max}=g(N_{screw}, L_{inner}, L_{plate}, E_{implant})$, $\sigma_{screw\_max}=g(L_{inner}, N_{screw}, L_{out})$, $k_{torsion}=g(L_{inner}, E_{implant})$, and $\varepsilon_{shear}=g(d_{gap}, L_{inner}, E_{implant})$. The response surface of surrogate model shows a good fit with FEA results (FIG. 10).

DISCUSSION

This invention provides a novel individualized preoperative planning system used by surgeons to devise a personalized patient treatment plan considering fracture fixation biomechanics.

Finite element modeling with modularized blocks shows that it is an efficient method to perform computer experiments for fracture fixation constructs.

The output of the polynomial regression model shows good fitting with the FEA results in the range of high $R^2$ values (0.74-0.97). The polynomial regression model and correlation results indicate that the inner working length appears to be the most significant variables for the maximum von Mises stress of implants and the construct stability of fracture fixation. An increase in fracture gap size does not appear to substantially affect the stress distribution in the plate.

As discussed above, there are several important uses of surrogate models of biomechanics in orthopaedic surgeries such as fracture fixation. The first is insight into which design variables have the largest effects on resulting biomechanics of the fracture repair. For example, our results indicate that strain at the healing tissue is strongly influenced by $L_{inner}$ and $d_{gap}$, whereas implant stresses are strongly influenced by $L_{inner}$ and $E_{implant}$. Thus if a surgeon were concerned about potential implant failure in the highly loaded subtrochanteric fracture fixation in an obese patient, they would want to use a shorter $L_{inner}$ and stiffer implants. Second, these surrogate models enable prediction of important biomechanical variables. As an application of these surrogate models, it can be used for a brief estimation of biomechanical output of a fracture fixation construct using a spreadsheet. An orthopaedic surgeon or resident can perform a simple calculation with this spreadsheet during their selection of a fracture fixation. Third, these models can be used for quick multivariate data visualization such as with 3D graphics, glyph plots, and so on because they can help orthopaedic surgeons to understand the complicated statistical and physical concept of biomechanics of orthopaedic surgeries, and they do not require a computationally expensive cost. For example, the results show the interactions between parameters for response variables, as shown in FIG. 7. In torsion loading, more interaction between parameters is observed, compared to axial loading. Fourth, design optimization is an application of these surrogate models to determine design parameters and provide the optimized fracture fixation construct for appropriate fracture healing. For example, 20% cases of axial loading and 37% of torsion loading show the optimal range of strain magnitude, and 12% cases of axial loading and 2% of torsion loading show over 10% strain, which may cause bone resorption.

In the development of a response surface model, there are several alternative criteria to determine the optimum number of regressor variables such as Mallow's Cp, Akaike's Information Criterion (AIC), and Bayesian information Criterion (BIC). For the verification of the regression model selection method, the polynomial regression model with a $R^2$-based selection method used in the present invention are compared with other criteria. The comparison results show a similar number of regressors selected. Various other methodologies such as kriging models, Bayesian approach, neural network and multivariate adaptive regression spines can be used to develop surrogate models.

Additional parameters may be included as construct design variables, such as various bone shapes, material properties of bone, bone density and boundary conditions. For example, bone density may have effects on the mechanical stability of a locked plating fracture fixation. Because FIA models are based on the immediate post-operation period, the assumption is that there is no significant biological healing process and the fracture fixation construct is modeled without tissue.

Various implants may be selected, for instance, unlocking screws, cannulated screws and unsymmetrical screw configurations. Additional output variables may be included as one of the finite element model outputs, for example, principal stress, and the location of maximum stress.

The invention claimed is:

1. A computer-implemented method for designing bone fracture fixation constructs for personalized surgical planning, the fracture fixation constructs design having design parameters as inputs and biomechanics as outputs, the method comprising:
   a. receiving, at the computer, individual patient imaging data including geometry of a fractured bone;
   b. presetting, by a user, a model of the fractured bone that represents the individual patient's data;
   c. presetting, by a user, biomechanics criteria, defining an appropriate treatment;
   d. presetting, by the user, the design parameters based on the individual patient data and a plurality of possible treatments;
   e. calculating, at the computer, biomechanics corresponding to the plurality of possible treatments, the calculated biomechanics being mapped graphically using three-dimensional bodies and three-dimensional field plots;
   f. comparing the calculated biomechanics with the preset biomechanics criteria;
   g. adjusting, by the user or the computer, the design parameters based on the comparison;
   h. repeating the steps e-g until the difference between the calculated biomechanics and the preset biomechanics criteria is less than a preset threshold; and
   i. outputting the design parameters for the fracture fixation constructs.

2. A computer-implemented method for designing individualized fracture fixation constructs according to claim 1, wherein the individual patient data further includes one or more of the following: bone density, bone shape, soft tissue anatomy, patient age, sex, weight, smoking status.

3. A computer-implemented method for designing individualized fracture fixation constructs according to claim 1, wherein the model of the fractured bone is a finite element model.

4. A computer-implemented method for designing individualized fracture fixation constructs according to claim 1, wherein the model of the fractured bone is selected from an existing collection of models that represent variations across a patient population.

5. A computer-implemented method for designing individualized fracture fixation constructs according to claim 1, further comprising:

after the step a, constructing an image-based modularized-block finite element model of the fractured bone based on the geometry; and automatically constructing finite element models of a plurality of fracture fixation constructs with design variations based on the image-based modularized-block finite element model of the fractured bone.

6. A computer-implemented method for designing individualized fracture fixation constructs according to claim 1 including the step of developing a surrogate model relating the design parameters to the biomechanics outputs.

7. A computer-implemented method for designing individualized fracture fixation constructs according to claim 1, wherein the design parameters and the calculated biomechanics are plotted with multivariate plots, wherein the user is able to specify data points or ranges by clicking within the multivariate plots and the computer is operable to identify the fracture fixation constructs that correspond to the specified data points or ranges clicked by the user within the plots.

8. A computer-implemented method for designing individualized fracture fixation constructs according to claim 1, wherein the computer identifies candidates for optimal fixation constructs based on searching the results of the plurality of simulated designs or use of the surrogate models.

9. A computer-implemented method for designing individualized fracture fixation constructs according to claim 1, wherein the fixation construct is a plate fixated on a fractured bone with screws.

10. A computer-implemented method for designing individualized fracture fixation constructs according to claim 9, wherein the design data includes one or more of plate length, fracture gap size, number of the screws, positions of the screws and plate material.

11. A computer-implemented method for designing individualized fracture fixation constructs according to claim 9, wherein the biomechanics output includes maximum stresses of the plate and the screws, stiffness of fracture fixation and strain at the fracture gap.

12. A computer-implemented method for designing individualized fracture fixation constructs according to claim 1, wherein the design parameters include parameters defining a custom designed implant.

13. An individualized preoperative planning system for designing fracture fixation constructs based on individual patient data, comprising:

an input for receiving individual patient imaging data, design parameters and biomechanics criteria of designs from a user;

a database for storing the fixation construct designs including the design parameters and biomechanics criteria; and a programmed computer for processing the patient data, the design parameters and the corresponding biomechanics and providing patient-optimized fracture fixation construct designs, the programed computer operable to;

a. calculate biomechanics corresponding to a plurality of possible treatments, the calculated biomechanics being mapped graphically using three-dimensional bodies and three-dimensional field plots;

b. compare the calculated biomechanics with the preset biomechanics criteria;

c. adjust, by the user or the computer, the design parameters based on the comparison;

repeat the steps a-c until the difference between the calculated biomechanics and the preset biomechanics criteria is less than a preset threshold; and output the design parameters for the fracture fixation constructs.

14. An individualized preoperative planning system according to claim 13, wherein the programmed computer is further operable to develop surrogate models for relating the design parameters to the biomechanics outputs.

15. An individualized preoperative planning system according to claim 13, wherein the programmed computer is further operable to perform a large number of finite element simulations based on a plurality of variations of the design parameters.

16. An individualized preoperative planning system according to claim 13, wherein the fixation construct is a plate fixated on a fractured bone with screws.

17. An individualized preoperative planning system according to claim 16, wherein the design data includes one or more of plate length, fracture gap size, number of the screws, positions of the screws and plate material.

18. An individualized preoperative planning system according to claim 16, wherein the biomechanics output includes one or more of the maximum stresses of the plate and the screws, stiffness of fractures fixation and maximum shear strain at the fracture gap.

* * * * *